US006773600B2

(12) United States Patent
Rosenblatt et al.

(10) Patent No.: US 6,773,600 B2
(45) Date of Patent: Aug. 10, 2004

(54) USE OF A CLATHRATE MODIFIER, TO PROMOTE PASSAGE OF PROTEINS DURING NANOFILTRATION

(75) Inventors: Barry P. Rosenblatt, Morrisville, PA (US); Richard C. Siegel, Chester Springs, PA (US)

(73) Assignee: Cantocor, Inc., Malvern, PA (US)

( * ) Notice: Subject to any disclaimer, the term of this patent is extended or adjusted under 35 U.S.C. 154(b) by 0 days.

(21) Appl. No.: 10/454,089

(22) Filed: Jun. 4, 2003

(65) Prior Publication Data

US 2003/0230532 A1 Dec. 18, 2003

Related U.S. Application Data

(60) Provisional application No. 60/394,733, filed on Jun. 14, 2002.

(51) Int. Cl.[7] .......................... B01D 61/20; B01D 37/00; A61K 39/395; C07K 16/34
(52) U.S. Cl. ..................... 210/639; 210/644; 210/651; 210/739; 210/743; 210/749; 424/176.1; 436/177; 436/178; 530/414
(58) Field of Search ................................. 210/639, 644, 210/650, 651, 652, 739, 743, 749, 767; 424/176.1; 436/177, 178; 530/387.1, 390.1, 414

(56) References Cited

U.S. PATENT DOCUMENTS 4,789,482 A    12/1988  DiLeo et al.
6,096,872 A     8/2000  Van Holten et al.

FOREIGN PATENT DOCUMENTS

WO    WO 96/00237 A1    1/1996
WO    WO 96/37086 A1    8/1998

OTHER PUBLICATIONS

Dielo, Vacante, Deane, "Size Exclusion Removal of Model Mammalian Viruses Using a Unique Membrane System, Part 1: Membrane Qualification," Biologicals: 1993: 21, 275–286.
Dielo, Vacante, Deane, "Size Exclusion Removal of Model Mammalian Viruses Using a Unique Membrane System, Part II: Modular Qualification and Process Stimulation," Biologicals: 1993: 21, 287–296.
Dileo, Allegrezza, Jr, "Validatable virus removal from protein solutions," Nature 1991: 351, 420–421.
Nel, Oppenheim, Rodgers, Effects of Solution Properities on Solute and Permeate Flux in Bovine Serum Albumin–IgG Ultrafiltration. Biotechno. Prog. 1994: 10, 539–542.

*Primary Examiner*—John Kim

(57) ABSTRACT

The invention relates to the field of protein purification and the recovery of large proteinaceous material through small, nanometer sized, pore exclusion filters for removal of contaminants such as viral pathogens.

7 Claims, 1 Drawing Sheet

Viresolve and Concentration / Diafiltration Process

Viresolve and Concentration / Diafiltration Process

Figure 1:
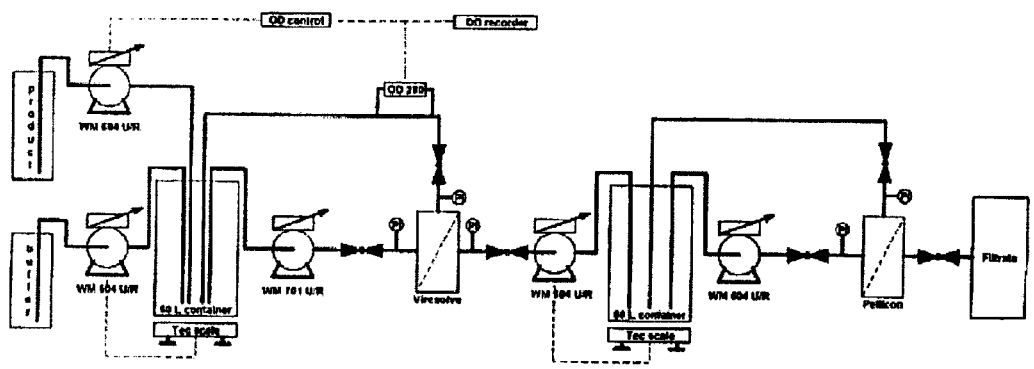

USE OF A CLATHRATE MODIFIER, TO PROMOTE PASSAGE OF PROTEINS DURING NANOFILTRATION

CROSS REFERENCE TO RELATED APPLICATION

This application claims the benefit of U.S. Provisional Application Serial No. 60/394,733, filed Jun. 14, 2002.

FIELD OF THE INVENTION

The invention relates to the field of protein purification and the recovery of large proteinaceous material through small, nanometer sized, pore exclusion filters for removal of contaminants such as viral pathogens. The invention relates to the use of additives to promote solubility of proteins in solutions being filtered for the purpose of removing pathogens, particularly viral pathogens, and has particular applicability to the purification of large proteinaceous biomolecules such as immunoglobulins.

BACKGROUND OF THE INVENTION

Liquid and gas separation processes are well known in the art. Most common separation processes involve a phase change, which increases the cost of the processes and often requires excessive temperature changes which can alter the product. Membrane separations, however, can achieve desired levels of separation without a change in the substances' phase. In essence, membrane separation selectively forces one or more substances through pores of a filter, leaving one or more larger substances behind. This process is often repeated with diminishing filter pore sizes until a satisfactory level of separation is achieved.

The use of nanofiltration to remove contaminants such as virus particles from parenteral protein products is based upon the ability of a filter of defined pore size to allow a soluble protein to pass through while denying passage of the larger viral particles (DiLeo, A J, et al, BioTechnology 1992, 10: 182,188.) Removal of virus from large biomolecules such as immunoglobulins (monoclonal or polyclonal antibodies), by size exclusion, is hindered by the difficulty of passing the large biomolecules through pore sizes of nanometer size, typically 12–15 nm. While a protein in solution, even one as large as an immunoglobulin, is expected to have a molecular radius much smaller than a viral particle, several factors can lead to an effective reduction in pore size and sieving coefficient. Some of these factors are due to interactions between the protein and the filter surface resulting in build up on the membrane surface known as a gelation or polarization layer. Other factors, such as protein self-association or aggregation, cause the protein to be trapped by the filter due to formation of masses too large to pass through the filter pores or that have surface characteristics that exhibit affinity for the membrane surface or pore surfaces causing them to adhere to the membrane instead of passing through.

International patent application, WO 9600237, describes methods for successful nanofiltration using pore sizes as small as 15 nm to filter purified proteins of molecular weight less than 150 kDa. WO 9600237 discloses the use of salt concentrations lying in the range from about 0.2 M up to saturation of the solution in virus-filtering of proteins, polysaccharides, and polypeptides to increase sieving coefficients. The advantage of the salt is stated by the applicants to be because the "protein contracts" and more easily passes through the filter. The use of a high salt content according to this method is also suggested to enable the use of "dead-end" filtering with membranes having pore sizes of 5–30 nm. Dead-end filtering refers to the practice of using a single pump to force fluid through the membrane from the surface. Dead-end filtration is simpler and more cost effective than tangential filtering process wherein a first pump maintains constant flow rate at the surface of the membrane and a second pump draws the protein through the filter by creating a negative pressure (suction) at the back of the membrane.

U.S. Pat. No. 6,096,872 recognized the utility of adding surfactants along with high ionic strength buffering during nanofiltration to remove viruses from immunoglobulin containing solutions in order to reduce protein dimerization, trimerization and aggregation, the teachings of which are hereby incorporated herein by reference.

It is also generally known that in order to reduce the interaction of a substance with the membrane surface, the "zeta-" or "z-"potential of the membrane surface should not be electrically attractive to that substance and altering the charge properties of the membrane can minimize surface precipitation. For example, U.S. Pat. No. 6,177,011 teaches that the neutralization of surface charges measured as zeta potential can reduce surface adsorption of membrane-fouling substances during reverse osmosis filtration processes where the substance carries a charged group. Changes in pH and salt concentration are other means of altering the z-potential of both the solutes and the membrane surface. In some cases, however, the manipulation of the z-potential by the addition of salt is counter-productive, resulting in an increase in soluble aggregation and an increase in the hydrophobic character of the membrane surface which may promote interaction with hydrophobic protein regions. Pall, et al (Colloids and Surfaces 1 (1980), 235–256.), reported that the phenomenon of removal of particles smaller than the pores of a filter is due to adherence of the particles to the pore walls under conditions wherein the particles and the pore walls are oppositely charged or alternatively wherein the zeta potential of the particles and the pore walls of the membrane are both low. Zierdt (Applied and Environmental Microbiology, (1979) 38:1166–1172) attributed the aforementioned phenomenon to electrostatic forces. Furthermore, these modifications do not address the effects of molecular geometry or protein aggregation in solution on membrane filtration.

In addition to the considerations of buffer components and their concentrations, care must be take to maintain the protein to be filtered in a concentration appropriate to maintaining good flow and minimal transmembrane pressure across the filter. WO 9837086 teaches the addition of buffer to the retentate in order to maintain transmembrane pressure during tangential flow of a pretreatment step to remove proteins having a molecular weight greater than that of the product protein(s). WO 9837086 further notes that nanofiltration is limited to therapeutic proteins having a molecular weight up to 150 kDa. Immunoglobulin G molecules are composed of two heavy chains and two light chain polypetides all covalently linked and have an average molecular weight of about 180 kDa. U.S. Pat. No. 6,096,872 seeks to address the problem of how to filter viruses from IgG products by including a non-ionic excipient with relatively high (physiological which is about 300 mOsm) ionic strength buffer. The use of high ionic strength buffers, however, may lead to protein aggregation or create the problem of salt removal from the product formulation. U.S. Pat. No. 6,096,872 teaches and claims a second nanofiltration step to concentrate the immunoglobulin and collect it in a low ionic strength buffer.

These methods suffer from various disadvantages, particularly in their efficiency. It is therefore the object of the present invention to overcome the short-comings of the prior art, particularly in developing a system for efficiently filtering pathogenic viruses from immunoglobulin products, thereby providing virally cleared, pure immunoglobulin for injection.

The molecular configuration or size of a protein species has been predicted by changes in the partial specific volume and self-association of proteins. The change in partial specific volume of proteins so modified has been demonstrated by the independent measurements of sedimentation coefficients using analytical centrifugation. The method described herein uses the addition of a clathrate modifying substance to modify the molecular configuration of the protein to minimize specific volume and aggregation thereby enhancing passage of the protein through the membrane in a nanofiltration process.

SUMMARY OF THE INVENTION

The method of the invention maximizes protein passage during membrane filtration by using buffer additives aimed to increase the hydrophobicity of the membrane surface and decrease the hydrodynamic radius of the protein as well as reduce the tendency for the self-association of the protein desired to be filtered. The method of the invention first maximizes protein passage by decreasing the pH and the salt of the buffer which increases the hydrophobicity of the membrane surface and decreases the hydrodynamic radius of the protein. Secondly, a clathrate modifer is included in the buffer which modifier decreases the hydrodynamic radius of the protein while minimizing the tendencies for the protein to associate with either itself or the membrane filter. Thirdly, the process optionally includes continuous in-line monitoring of the filtration in order to maintain the above parameters of pH and clathrate modifier constant while maintaining low local levels of soluble protein. The use of the methods of the invention result in an increase in sieving coefficient and the ability to maintain reduced trans-membrane pressure during virus particle filtration. The process is applicable to the purification of any large proteinaceous biomolecule, particularly immunoglobulins. The immunoglobulins may be a monoclonal or polyclonal immunoglobulin.

The clathrate modifier is perferably a polyol sugar or sugar alcohol having from 4 to 8 hydroxyl groups. Examples of preferred polyols are sugars, including mono-saccharides and disaccharides preferably sucrose. The concentration of the polyol used as a clathrate modifier will generally be 5% w/v or greater. The use of sucrose causes a decrease in the size of the molecule and a reduction in the tendency for self-association of the protein desired to be freed from virus particles.

Thus, the invention contemplates a method for purifying a proteinacious material such as an immunoglobulin comprising the steps of:

(a) admixing the proteinaceous material with:
 (i) a low pH, low conductivity buffer solution formulated to reduce the pH between 5.0 and 6.0, and to achieve an ionic strength of less than 30 mS/cm;
 (ii) a non-ionic surfactant; and
 (iii) a clathrate modifier;
(b) performing nanofiltration on the proteinaceous material to obtain a purified material substantially free of viral particles.

Preferably, the clathrate modifier is a polyol sugar or sugar alcohol having from 4 to 8 hydroxyl groups.

The method of the invention may also include conducting an in-line pre-filtering step and monitoring the concentration of the material by installing an in-line concentration controlling monitor to maintain the parameters of pH, and protein concentration within pre-set ranges optimal for the material being purified.

BRIEF DESCRIPTION OF THE DRAWINGS

FIG. 1. Is a schematic representation of the vessels and monitoring equipment used in nanofiltration and the direction of fluid flow.

DETAILED DESCRIPTION

The instant invention uses a combination of selection of buffer, non-ionic surfactant and the use of a clathrate modifier as processing aids during viral reduction or viral clearances using size exclusion nanofiltration for purification of large proteinaceous biomolecules. The invention allows a small pore size exclusion nanofilter to be used with a globular protein molecule such as an immunoglobulin in a manner which allows for efficient flowthrough, minimal yield loss and no significant change in the immunoglobulin characterization aggregate level or stability.

Virus removed from the proteinaceous material by the nanofiltration method of the invention include all potential categories of virus, both enveloped (for example HIV, Hepatitis B) and non-enveloped (for example Hepatitis A, Parvovirus B19).

The advantages of the use of the processing aids and the method of the present invention include:

(1) the reduction of processing time and increased yield since the conditions employed increase the hydrophobicity of the membrane surface and reduce the specific volume and aggregation of the proteinaceous material;
(2) the ability to use smaller pore size nanofilters, thereby ensuring removal of smaller size viral particles;
(3) the process can be automated for continuous monitoring to allow for maximum efficiency and highest product yield per filter area;
(4) the essential characteristics of the proteinaceous material are unaffected by the process maintaining the integrity and quality of the end product.

In a broad sense, a clathrate is a molecular association in which the result may form a particle. Clathrates are included among those complexes in which one component (the host) forms a cavity or, in the case of a crystal, a crystal lattice containing spaces in the shape of long tunnels or channels in which molecular entities of a second chemical species (the guest) are located. There is no covalent bonding between guest and host, the attraction being generally due to van der Waals forces. If the spaces in the host lattice are enclosed on all sides so that the guest species is "trapped" as in a cage, such compounds are known as "clathrates" or "cage" compounds". van der Waals forces and hydrophobic interactions bind the guest to the host molecule in clathrates and inclusion compounds. Examples of hydrogen-bonded molecules that form clathrates are hydroquinone and water, and host molecules of inclusion compounds, urea or thiourea.

In the present case, the term "clathrate modifier" means a substance that is capable of modifying the clathrate structure of a protein in an aqueous environment and reducing its overall specific volume. Substance such as large globular proteins are good candidates for clathrate modifiers because of their capability of forming hydrogen bonds in an aqueous environment. The polyol clathrate modifier of the present invention, modifies the clathrate complex of the proteinaceous material thereby reducing its specific volume and allowing for a reduction in processing time and greater flowthrough in the nanofiltration process.

In this specification by "polyol sugars and sugar alcohols" is meant a group of polyols having from 4 to 8 hydroxyl groups. Examples of preferred polyols are sugars, including monosaccharides and disaccharides, and sugar alcohols as well as derivatives thereof having from 4 to 8 hydroxyl groups.

Examples of monosaccharides having 4 hydroxyl groups are arabinose, ribose and xylose. An example of a sugar alcohol having 4 hydroxyl groups is the sugar alcohol derived from erythrose, i.e. erythritol.

Examples of monosaccharides having 5 hydroxyl groups are galactose, fructose, glucose and sorbose. An example of a sugar alcohol having 5 hydroxyl groups is the sugar alcohol derived from xylose, i.e. xylitol.

Examples of sugar alcohols having 6 hydroxyl groups are those derived from glucose and sorbose as well as from the hydrolysis products of sucrose, e.g. sorbitol and mannitol. Examples of disaccharides are maltose, lactose and sucrose, the latter being preferred, all of which contain 8 hydroxyl groups.

The large proteinaceous material which may be processed in accordance with the present invention include large globular proteins such as immunoglobulins (for example IgG) and fragments thereof, blood coagulation factors, growth hormones, apolipoproteins, enzymes and similar protein biomolecules, whether naturally occurring or genetically engineered.

The term "z-potential," as used herein, means surface charge. The surface charge of a particle is sometimes referred to as its z-potential, a measurement of charge which falls off with distance. The z-potential is directly correlated with the polarity or net charge of a compound.

As used herein, the term "nanofiltration" refers to filtration using size exclusion means where the pore size is of nanometer size. In general, the pore size of the nanofiltering units, also referred to as UF filters, employed in the production of substantially pure, virus-free immunoglobulin products of the instant invention is less than about 30 nm, most preferably less than about 15 nm. However, any membrane having the filter cutoff rating sufficient to reduce or eliminate non-enveloped virus from a proteinaceous solution can be employed in the processing methods of the invention. For example, the VIRESOLVE® 180 SYSTEM Ultrafiltration System (Millipore Corporation, Bedford, Mass.) unit may be employed, such unit having a molecular weight pore size rating of less than about 180 KD molecular weight or about 12 nm.

The nonionic surfactant or detergents which may be used in the present invention include the nonionic polyoxyethylene detergents for example the polysorbates, TWEENS; vinyl polymers, PLURONICS; polyoxyethylene-polypropylene polymers or co-polymers; Brij, Sterox-AJ, and Tritons. Most preferred is polyoxyethylene sorbitan monooleate, polysorbate 80 (TWEEN 80).

The buffer employed in the invention is selected from any suitable low pH, low conductivity buffer such as phosphate buffers, citrate buffers, borate buffers, acetate buffers and glycine buffers at a pH of about 5.0. The buffer is employed to maintain the pH below 6 and reduce aggregation of the protein thereby allowing more efficient flow, through the nanofilter. Preferably a buffer with a low ionic strength of 50 mM±/−20% is employed, preferably a sodium acetate buffer, pH 5.0.

The method involves transferring the protein of interest into a low pH (pH 5.0–6.0), low conductivity buffer (10–20 mS/cm), containing a non-ionic detergent such as TWEEN 80 at a concentration of 0.01% and sucrose at a concentration of between 5 and 10% w/v. The tangential flow apparatus is in fluid communication with several other vessels: a product tank, a buffer tank, and a feed/recirculation tank equipped with an agitator. The relationship of these vessels and the fluid flow between is shown in FIG. 1.

The protein concentration used in the processing of the instant invention will be in the range of about 0.1% to about 1% by weight. Up to about 1% can be used when the protein is monomeric or monoclonal. For immunoglobulins such as a chimeric monoclonal IgG1, the initial protein concentration used for processing is about 1 to 10 mg/ml.

During processing and filtration, the protein concentration is preferably monitored to maintain optimal levels. As shown in FIG. 1, this can be accomplished by the installation of an in line concentration monitor. A dead-end prefilter may be placed in the line between the feed/recirculation tank and the UF filter. A UV monitor is placed in-line between the UF filter and recirculation tank, on the retentate line. to provide a feed-back to the feed and buffer addition tanks to allow maintenance of the target protein concentration. Adjustment of the prefiltered product containing solution is achieved by the addition of buffer into the feed/recirculation tank to achieve the desired pH, conductivity, detergent concentration, and sucrose concentration. FIG. 1 shows the fluid flow from the feed/recirculation tank. During the filtration, the concentration of the retentate is kept constant by the addition of buffer in order to minimize protein-protein interaction. In the example shown, this is accomplished by control of the pumps supplying the product into the recirculation tank. By increasing/decreasing the speed of the pump, the concentration can be kept within a narrow specified range. A load cell under the recirculation tank is used as an addition feedback to the buffer pump to avoid overflowing the tank.

During filtration, the transmembrane pressure is preferably in the range of 0.2 to about 2.0 bar, most preferably maintained at less then about 1.0 bar. The sieving coefficient will preferably be in the range of 75–95% with excursions no lower than 60%.

EXAMPLE

A working example of this invention is demonstrated in the production of a chimeric human/mouse IgG1. The protein, after elution from a cation exchange column at pH 5.0, is placed in the product tank. The buffer tank is filled with 50 mM Sodium acetate, 6% sucrose, 0.01% polysorbate (tween) 80. The protein and buffer are mixed to achieve a final protein concentration of 2.0 ∀0.2 mg/mL in the feed tank. The filtration is started with a cross flow rate of xx mL/min/cm$^2$ and a permeate rate of no greater than yy mL/min/cm$^2$. Transmembrane pressure and retentate concentration is monitored to ensure that the process remains within the prescribed limits. Once the product tank is empty, the filters are rinsed with 3× the hold-up volume of the system to maximize the yield.

What is claimed is:

1. A method for purifying a proteinacious material comprising the steps of:
   (a) admixing the proteinaceous material with:
      (i) a low pH, low conductivity buffer solution formulated to reduce the pH between 5.0 and 6.0, and to achieve an ionic strength of less than 30 mS/cm;
      (ii) a non-ionic surfactant; and (iii) a clathrate modifier;
(b) performing nanofiltration on the proteinaceous material to obtain a purified material substantially free of viral particles.

2. The method of claim 1 wherein the proteinaceous material is an immunoglobulin.

3. The method of claim 1 wherein the clathrate modifier is a polyol sugar or sugar alcohol having from 4 to 8 hydroxyl groups.

4. The method of claim 3 wherein the polyol is a monosaccharides or disaccharides.

5. The method of claim 4 wherein the polyol is sucrose.

6. The method of claim 1 wherein the concentration of the polyol used as a clathrate modifier is about 5% w/v or greater.

7. A method for purifying a proteinacious material comprising the steps of:
   a) admixing the proteinaceous material with a buffer solution:
   adjusting the pH and the ionic strength of the buffer such that the pH is 5.0–6.0 and the ionic strength is less than 30 mS/cm;
   b) adding a surfactant to the buffer to minimize protein-protein and protein-membrane interactions,
   c) adding a clathrate modifier to the buffer, which clathrate modifier
      i) Reduces the hydrodynamic radius of the protein and
      ii) Minimizes the self-association of the protein;
   d) installing an in-line prefilter to the system;
   e) installing an in-line concentration controlling monitor to the system; and
   f) using information from the in-line concentration controlling monitor to maintain the buffer parameter of pH and protein concentration within the range of pH of 5.0–6.0 and the ionic strength is less than 30 mS/cm.

* * * * *